United States Patent
Houge et al.

(10) Patent No.: US 6,750,447 B2
(45) Date of Patent: Jun. 15, 2004

(54) CALIBRATION STANDARD FOR HIGH RESOLUTION ELECTRON MICROSCOPY

(75) Inventors: Erik Cho Houge, Orlando, FL (US); Catherine Vartuli, Windermere, FL (US); John Martin McIntosh, Orlando, FL (US); Fred Anthony Stevie, Orlando, FL (US)

(73) Assignee: Agere Systems, Inc., Allentown, PA (US)

( * ) Notice: Subject to any disclaimer, the term of this patent is extended or adjusted under 35 U.S.C. 154(b) by 0 days.

(21) Appl. No.: 10/122,645

(22) Filed: Apr. 12, 2002

(65) Prior Publication Data

US 2003/0193022 A1 Oct. 16, 2003

(51) Int. Cl.[7] .............................................. G12B 13/00
(52) U.S. Cl. ..................................... 250/252.1; 250/311
(58) Field of Search ...................... 250/252.1, 306–307, 250/310–311

(56) References Cited

U.S. PATENT DOCUMENTS

| | | | |
|---|---|---|---|
| 4,068,381 A | * | 1/1978 | Ballard et al. ................ 33/1 R |
| 4,386,850 A | * | 6/1983 | Leahy ..................... 356/243.4 |
| 5,602,323 A | | 2/1997 | Ohmi |
| 5,825,498 A | | 10/1998 | Thakur et al. |
| 5,981,119 A | | 11/1999 | Adams |
| 6,231,668 B1 | | 5/2001 | Loesch et al. |
| 6,238,940 B1 | | 5/2001 | Steffan et al. |
| 6,301,510 B1 | | 10/2001 | Cooperberg et al. |
| 6,326,619 B1 | | 12/2001 | Michael et al. |
| 2003/0025087 A1 | * | 2/2003 | Schamber et al. ....... 250/491.1 |
| 2003/0058437 A1 | * | 3/2003 | Tortonese et al. ........ 356/243.4 |

* cited by examiner

Primary Examiner—John R. Lee
Assistant Examiner—Christopher M. Kalivoda
(74) Attorney, Agent, or Firm—James H. Beusse; Beusse Brownlee Wolter Mora & Maire, P.A.

(57) ABSTRACT

A method and apparatus used to calibrate high-resolution electron microscopes where a single standard provides multiple samples, each having a different atomic structure, permits rapid accurate calibration of the entire range of magnifications. The different atomic structure dimensions possess known reference measurement data. The S/TEM is adjusted to focus onto the crystal lattice structure of each sample in a selected sequence. Measurements of these lattice spacings are compared to known dimensions. If S/TEM measurements do not agree with the lattice spacing dimensions, the S/TEM magnification is adjusted to reflect known dimensions. Typical standard exchange and associated processing steps are eliminated by the use of the single standard comprising of a plurality of samples.

12 Claims, 5 Drawing Sheets

CALIBRATION STANDARD FOR HIGH RESOLUTION ELECTRON MICROSCOPY

FIELD OF THE INVENTION

This invention relates to a method and apparatus used to calibrate a measuring instrument. More particularly this invention relates calibration of Scanning Transmission Electron Microscopes (STEM) and Transmission Electron Microscopes (TEM).

BACKGROUND OF THE INVENTION

Semiconductor manufacturing consists of a number of crucial processing steps performed on wafer lots where measurements of minimum feature sizes known as critical dimensions (CD) are made to ensure proper device fabrication. The high-degree of precision during this processing requires the utilization of Scanning Transmission Electron Microscopes and Transmission Electron Microscopes (S/TEM). These critical tools provide measurement capabilities in the low nanometer range. Accuracy of their measurements is essential since effective process controls depend on CDs they supply. S/TEMs require frequent calibration to ensure their accuracy since processing errors cause appreciable inconsistencies in CDs. Calibration procedures are very time consuming and have a negative impact on semiconductor fabrication workflow. Typical S/TEM magnification calibration approaches are also limited in accuracy.

A conventional calibration approach utilizes a standard (e.g., TEM grid) that possesses one crystal lattice specimen to calibrate a S/TEM for a particular magnification. This approach requires that calibration for each magnification of a range of magnifications required to support semiconductor fabrication use a different standard. Thus, numerous specimen exchanges along with new orientations to achieve calibration over a range of magnifications are required. In addition, the beam conditions must be reset for each standard. Measurements obtained from the specimen's crystal lattice spacing are compared to known data to determine if the S/TEM requires adjustment or if the magnification results being calibrated are within tolerance. Calibration adjustments are made accordingly. This iterative process is conducted until calibration is achieved for the full range of magnification required in support of semiconductor fabrication.

Another method using a scale with multiple crystal lattice specimens to calibrate a S/TEM is described in U.S. Pat. No. 6,231,668 to Loesch entitled "Method for Manufacturing a Calibrated Scale in the Nanometer Range for Technical Devices Used for the High Resolution or Ultrahigh-Resolution Imaging of Structures and Such Scale". This patent discloses utilization and manufacturing of a layered scale. Depositions of at least two different crystalline or amorphous materials are used to create the scale. These materials are deposited on a substrate in alternate layers, one on top of the other. Even though a plurality of crystal lattice materials are used, this scale results in a single multi-layered specimen also known as sample on a substrate so the range of calibration of magnification is still limited very limited.

A few other approaches allow calibration over a range of magnifications. However, these standards are limited and do not cover the entire range of S/TEM magnifications typically required to support current semiconductor fabrication requirements. Nor do these solutions provide the accuracy that can be achieved with known crystal lattice plane spacing. It would be very advantageous to utilize a standard that is comprised of a plurality of specimens each having or arranged to present a different lattice spacing or atomic spacing on a single TEM grid. Utilization of this standard would allow rapid accurate calibration of the S/TEM at all desired magnifications and conditions to overcome limitations of prior art. Then, fast thorough calibration can be performed streamlining workflow of a semiconductor processing line.

SUMMARY OF THE INVENTION

An object of the present invention is to streamline semiconductor fabrication workflow, solve the need for greater accuracy, and induce process reliability/repeatability by enabling rapid, accurate calibration of high-resolution electron microscopes.

Another object of the present invention is to provide a method and apparatus for rapid high-resolution electron microscopes calibration over the range of magnifications required utilizing a single standard that provides multiple specimens, each possessing different lattice spacing.

In accordance with the present invention, the disclosed method and apparatus enables a calibration process of an electron microscope to be performed where only one standard is required for calibration of the entire range of magnifications. The enabling apparatus consists of different atomic structures such as crystal lattice spacing samples also known as specimens that are resident on the single standard. These samples are arranged in a grid pattern. Lattice spacing dimensions of the samples are known reference data. The S/TEM is adjusted to establish viewing of a single sample from a plurality of samples by bring fringes of the lattice space into focus. Measurements of these lattice spacings are compared to known reference measurement data. If S/TEM measurements do not agree with the lattice spacing dimensions then, the S/TEM magnification is adjusted (i.e., the input current to the lens is adjusted) to reflect known reference data. Sequentially viewing one sample at a time and performing S/TEM adjustments for the particular sample accomplishes calibration. All samples required to support magnification calibration of a range of magnification are used.

BRIEF DESCRIPTION OF THE DRAWINGS

The features of the invention believed to be novel are specifically set forth in the appended claims. However, the invention itself, both as to its structure and method of operation, may best be understood by referring to the following description and accompanying drawings.

DETAILED DESCRIPTION OF THE INVENTION

Figure 1:
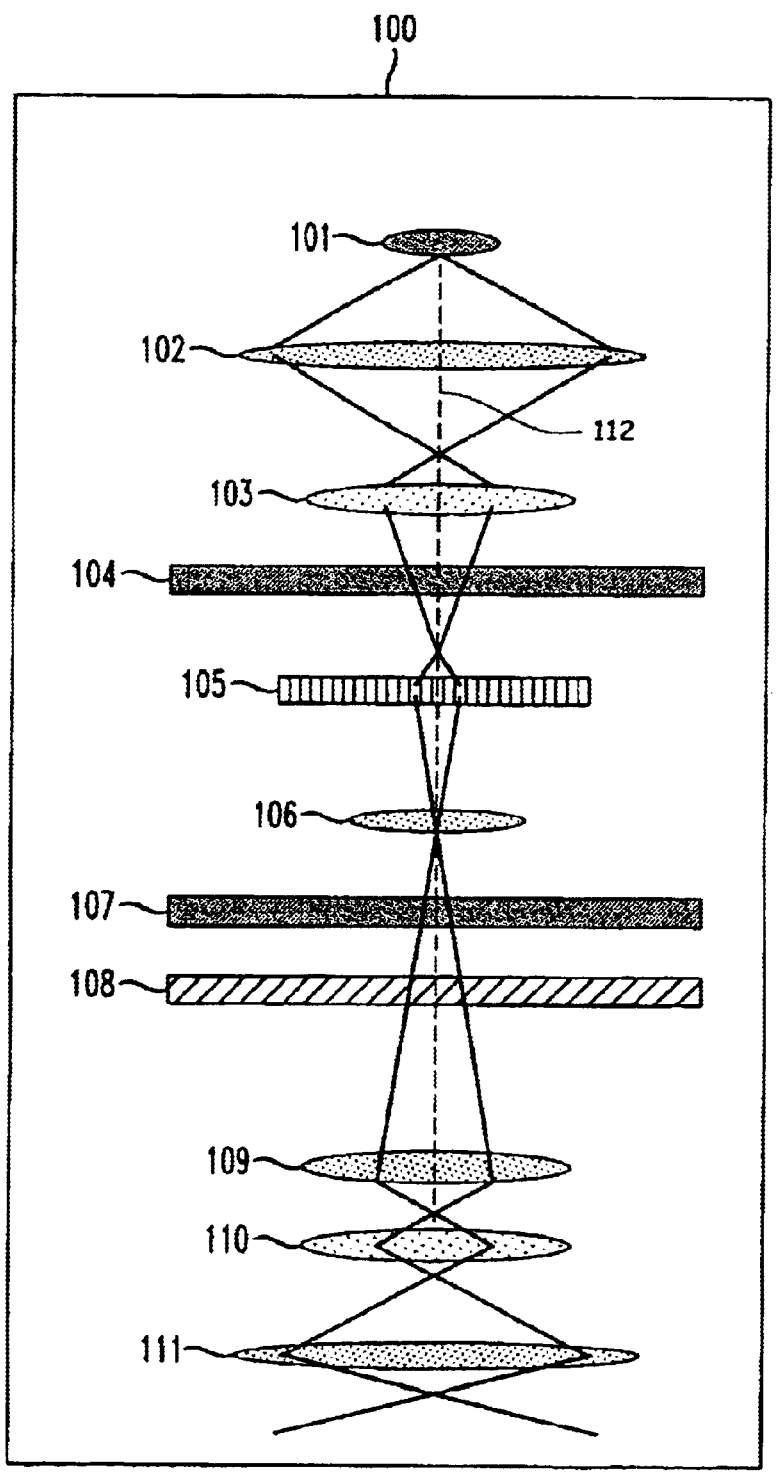
FIG. 1 is a diagram representing a prior art S/TEM system.

During fabrication, semiconductor products are analyzed using high-resolution electron microscopy such as Scanning Transmission Electron Microscopes (STEM) and Transmission Electron Microscopes (TEM), sometimes referred to collectively as S/TEM system. A block diagram representing a S/TEM system 100 is provided in FIG. 1 where the energy source represents an electron gun 101 that produces a stream of monochromatic electrons. This stream is focused onto a small, thin, coherent beam by the use of condenser lenses 102, 103. The first lens 102 largely determines the "spot size"; the general size range of the final spot that strikes a sample 105. A "spot size knob" usually controls this condenser lens. The second condenser lens 103 changes the spot size on a sample also known as a specimen 105, adjusting the beam from a dispersed spot to a pinpoint beam. An "intensity or brightness knob" controls this lens. The user selected condenser aperture 104 constricts the resulting beam. This condenser aperture 104 blocks high angle electrons, those far from the optic axis (i.e., the dotted line 112 down the center). The beam strikes a sample 105 and parts of it are transmitted through the sample. The transmitted portion is focused by the objective lens 106 into an image. The optional objective lens 107 and selected area 108 apertures can restrict the beam. The objective aperture 107 enhances contrast by blocking out high-angle diffracted electrons. The selected area aperture 108 enables a user to examine the periodic diffraction of electrons by ordered arrangements of atoms in the sample. The resulting image is enlarged as it passes through the intermediate lenses 109, 110 and projector 111 lens. This image strikes the phosphor image screen and light is generated, resulting in an image for the user to see. The darker areas of an image represent areas of the sample that fewer electrons were transmitted through (they are thicker or denser). The lighter areas of the image represent those areas of the sample that more electrons were transmitted through (they are thinner or less dense).

Semiconductor fabrication routinely requires S/TEM magnification ranging from 10,000 to 5 million times a sample size. Accuracy of S/TEM results at these magnification levels is critical to fabrication processing. Therefore, routine periodic S/TEM calibration must be performed. S/TEMs can be calibrated by measuring known lattice spacing of various materials. S/TEM calibration is typically an iterative process as indicated in the simplified prior art process flow diagram of FIG. 2. The process begins by starting the S/TEM system 100 along with setting operational parameters and S/TEM conditions 200 for a particular magnification. Beam alignment/optimization 201 is established for this desired magnification. The sample to be used for a particular magnification calibration is exchanged 202 (i.e., located and prepared for use in the S/TEM). The sample is orientated perpendicular to the beam and the beam optimized under the desired condition, in order to image the sample lattice or atomic structure. Liquid nitrogen is injected 203 to preclude contamination. Adjustments are made to focus the beam, block 204, onto the sample. Then, the S/TEM is calibrated appropriately, block 205, where measurements are obtained and compared with known values from reference data. S/TEM adjustments are made for any differences that are out of tolerance. Upon requiring calibration for another magnification 206, the process is repeated, 208. Standard samples are exchanged to calibrate a S/TEM at each of a range of magnifications required. Each time a sample is exchanged, S/TEM operational conditions and orientation must be reset, which is iterative and very time consuming. Once calibration is achieved for the complete magnification range required, the calibration procedure is considered complete, block 207. This process has a significant negative impact on fabrication cycle time (i.e., the S/TEM is not available for fabrication support while being calibrated).

Figure 2:
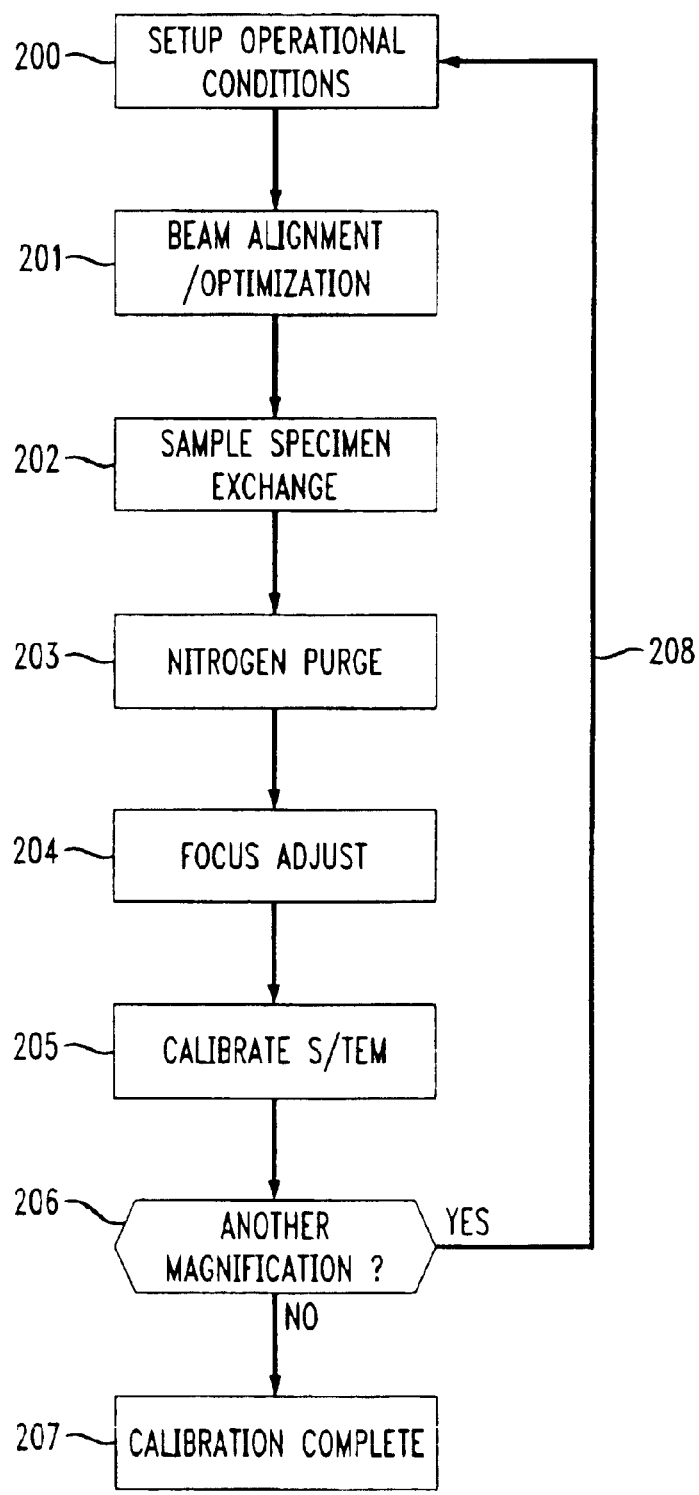
FIG. 2 is a flow diagram of a typical prior art calibration process.
Figure 3:
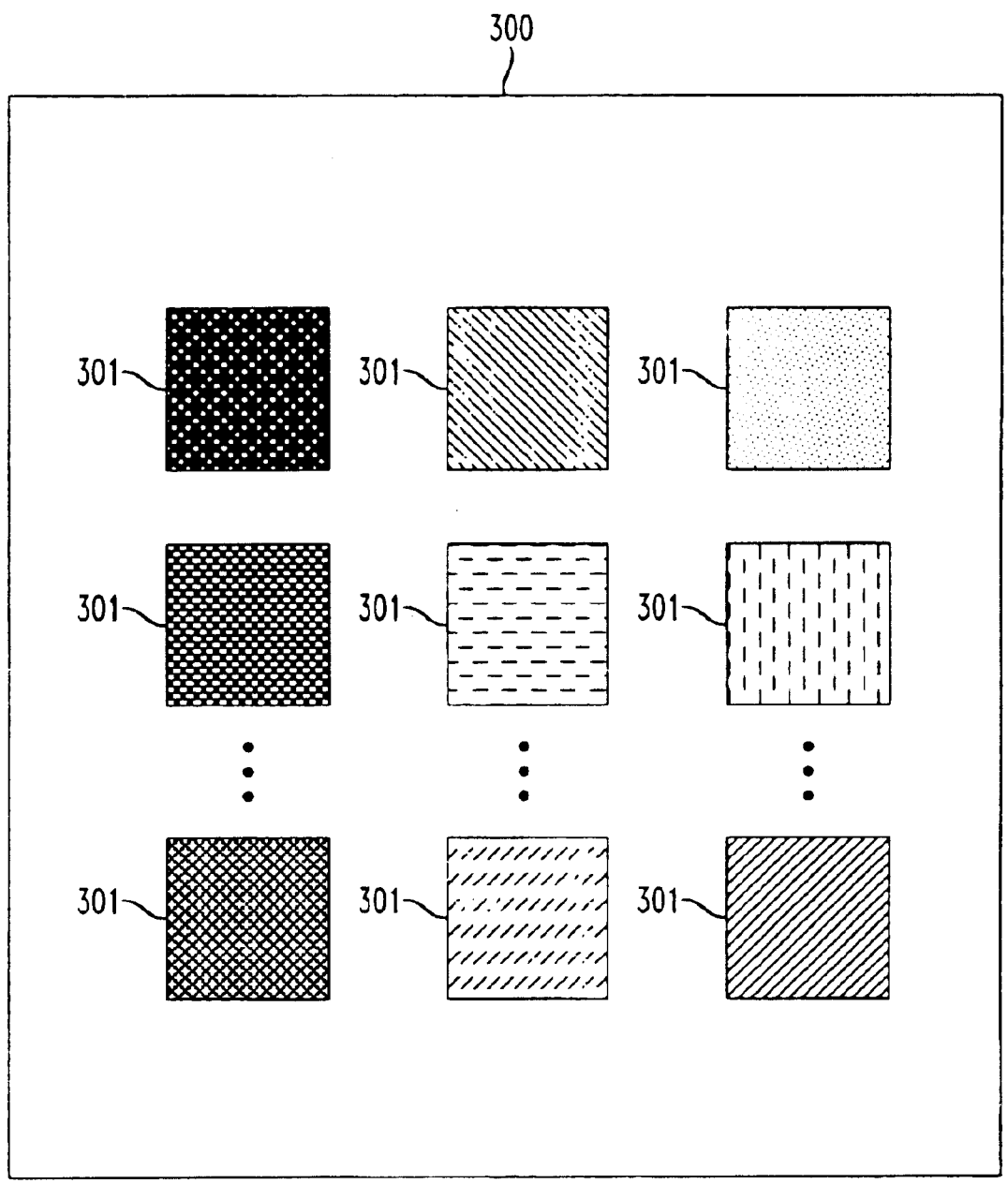
FIG. 3 is a block diagram of a calibration standard with multiple samples.

The invention disclosed streamlines the calibration procedure by alleviating the process iteration indicated in FIG. 2. A preferred embodiment utilizes a single standard for calibration over the range of magnifications required. A plurality of samples or specimens having different atomic structures is provided on the single standard as indicated in the block diagram representation of FIG. 3. Since the objective of having different samples is to have different lattice dimensions for calibration, it is recognized that some samples may be of the same material but oriented to present a different lattice or atomic structure to the electron beam. Multiple samples with different lattice spacing are provided on this single standard to calibrate the S/TEM. The block diagram is a representation of multiple, varying calibration specimens or samples 301 on a single substrate 300. In the preferred embodiment, each unique sample 301, has a known crystal lattice structure. with crystal lattice spacings that are very accurately known for each sample used. Each sample supports a specific S/TEM calibration magnification so that the entire range of magnifications required is accommodated with the one standard. Each sample is positioned independently in a respective defined region of the standard such that each sample can be selected for imaging.

A preferred embodiment of the calibration standard is comprised of a standard possessing multiple calibration samples having different crystal lattice planes where the interference fringes of each of the samples range from approximately 0.3 nanometers to 9.0 nanometers. The standard utilizes a carbon sheet sample support with a copper grid structure supporting the carbon sheet. Each grid section may be 10 by 10 nanometers and each sample may be 5×5 nanometers. Focused ion beam lift-out may be used to create a sample that is to be placed on the grid. Focused Ion Beam (FIB) lift-out allows multiple thinned samples to be obtained rapidly and to be placed on the grid. The carbon sheet support structure thickness is less than about 500 nanometers with a preference of less than about 100 nanometers. The thickness of each sample may be about 0.5 micrometers.

Figure 4:
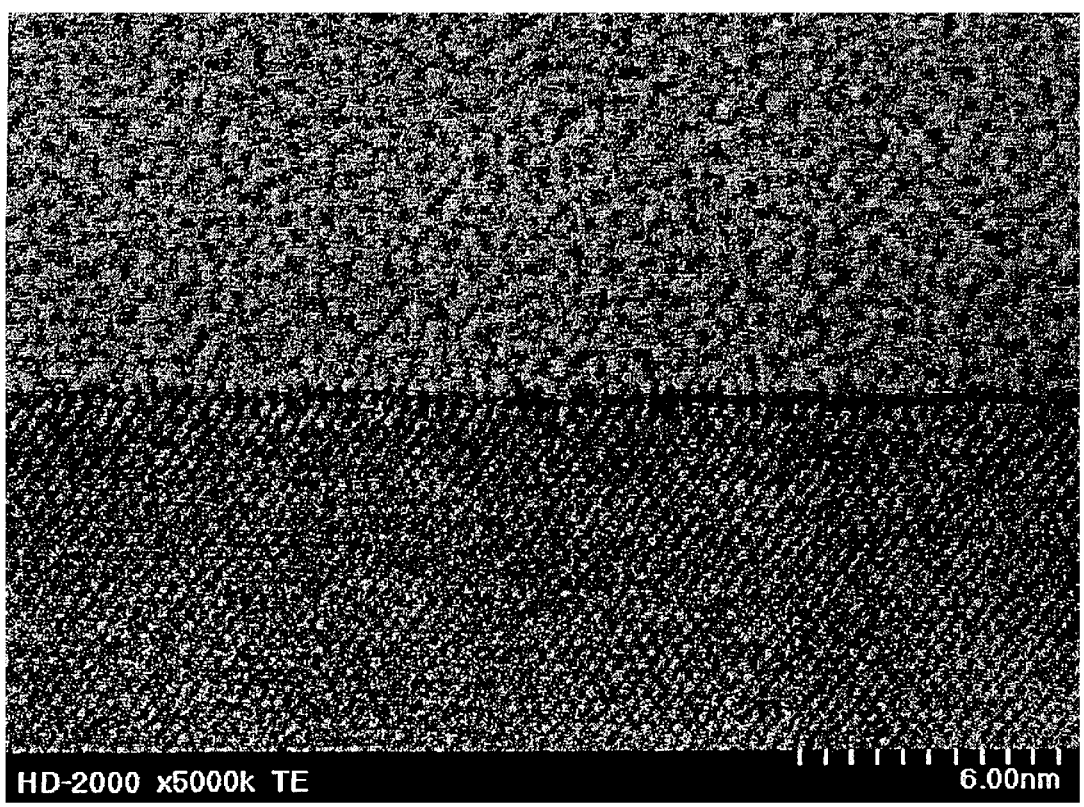
FIG. 4 provides S/TEM imagery of a plurality of crystal lattice samples on one standard.

FIG. 4 provides actual S/TEM imagery of two adjacent crystal lattice samples. These images are of S/TEM lattice fringes possessing high-resolution cross-fringes. In order to image lattice spacings in S/TEM, a very thin section of crystalline material is placed in the tool. The electron beam scans over the crystalline sample, and the electrons create interference fringes as they pass through the evenly spaced atomic planes. The pitch of the interference fringes will vary depending on the distance between the crystalline lattice planes. The pitch of the interference fringes is uniform and constant over time and differing beam conditions. The fringes are imaged, and their pitch is measured. Measurements on the sample of interest are compared with values from the known reference data, and the differences monitored. Any significant deviation is corrected during calibration.

Figure 5:
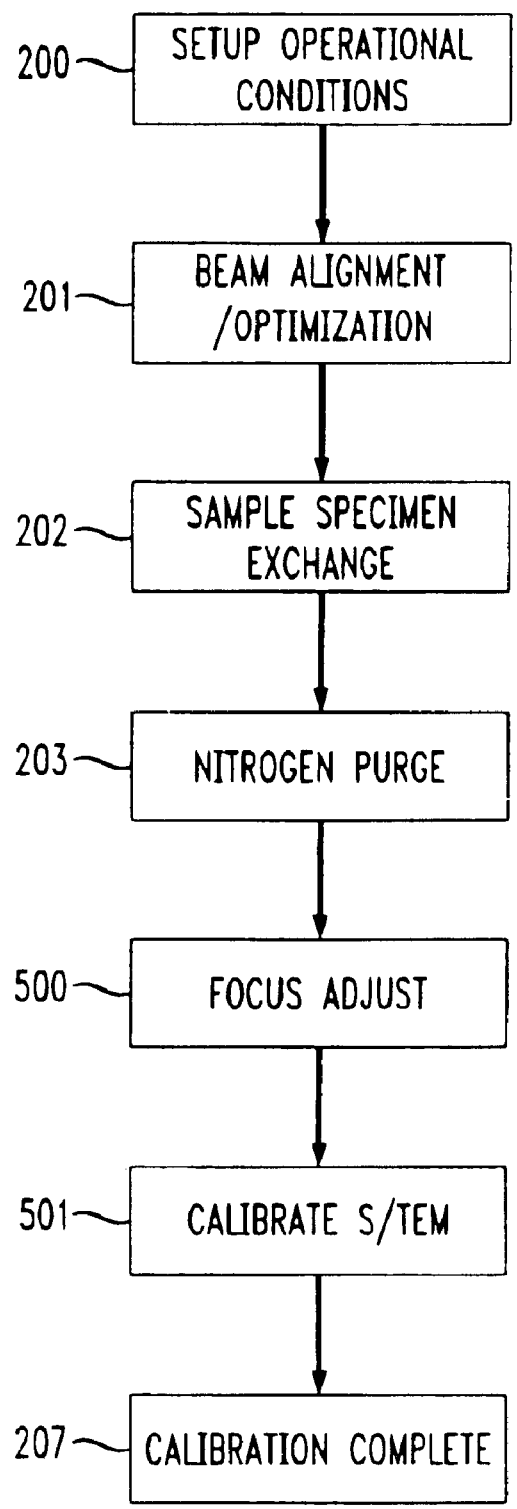
FIG. 5 is a flow diagram of the preferred embodiment optimized calibration process.

This invention establishes S/TEM calibration that can be performed accurately and quickly over the range of magnifications of the S/TEM, without the necessity of iterative standard exchanges and multiple sample/beam alignments. FIG. 5 depicts an optimized calibration process flow diagram leveraging the use of the single standard 300 of FIG. 3. By placing samples with a range of lattice or atomic spacings on the same sample (i.e., grid), sample exchange 202 along with nitrogen purge 203 are only performed once. By focusing, block 500, from sample to sample on the grid 300, various pitches can be observed at the appropriate magnifications. This ensures beam conditions remain the same from sample to sample and eliminates sample and beam alignment between samples. Viewing a sample can be accomplished by moving the ion beam or by moving the sample. Since the actual lattice spacing is known for each sample, the operator can move rapidly between samples to make the necessary calibration adjustments 501 and the calibration is then complete 207. The ease and speed of this calibration method affects not only the throughput of the S/TEM, but the frequency with which tests can be reasonably conducted. This process also speeds up turnaround time of samples for critical dimension measurements on features too small to be measured accurately in the clean room and for checks on in-line tools.

While only certain preferred features of the invention have been shown by way of illustration, many modifications and changes will occur to those skilled in the art. It is, therefore, to be understood that the present claims are intended to cover all such modifications and changes, which fall within the true spirit of the invention.

What is claimed is:

1. A method for calibrating a transmission electron microscope comprising:
   providing a calibration standard having a plurality of specimens positioned thereon, at least some of the specimens having a different atomic spacing;
   positioning the calibration standard in a viewing area of the transmission electron microscope; and
   sequentially viewing a plurality of the specimens and adjusting the calibration of the microscope for each specimen.

2. The method of claim 1 wherein the step of sequentially viewing includes the step of focusing the transmission electron microscope.

3. The method of claim 1 wherein the step of sequentially viewing includes the step of translating the standard to position selected specimens within a viewing range of the microscope.

4. The method of claim 1 wherein the step of sequentially viewing includes the step of electronically directing an electron beam of the microscope onto selected ones of the specimens.

5. A calibration standard comprising:
   a gridwork having a plurality of defined regions;
   a support structure bonded to the gridwork;
   a plurality of calibration samples, each sample having a different atomic spacing and being placed on a defined region of the gridwork on the support structure.

6. The calibration standard of claim 5 wherein the calibration samples are selected from a group of materials having crystal lattice planes in which the pitch of the interference of fringes of each of the samples ranges between about 0.3 nanometers to about 9.0 nanometers.

7. The calibration standard of claim 5 wherein the gridwork comprises a copper grid.

8. The calibration standard of claim 5 wherein the support structure comprises a carbon sheet.

9. The calibration standard of claim 5 wherein each of the calibration standards has a thickness of about 0.5 micrometers.

10. The calibration standard of claim 5 wherein the support structure has a thickness of less than about 500 nanometers.

11. The calibration standard of claim 10 wherein the support structure has a thickness of less than about 100 nanometers.

12. The calibration standard of claim 5 wherein the calibration samples have a crystal lattice structure varying between about 0.3 nanometers to about 9.0 nanometers.

* * * * *